United States Patent [19]

Kolb et al.

[11] 4,453,954

[45] Jun. 12, 1984

[54] ASSEMBLY FOR CONNECTING THE COLUMN ENDS OF TWO CAPILLARY COLUMNS

[75] Inventors: Bruno Kolb, Owingen; Peter Pospisil, Uberlingen; Maria Auer, Stockach, all of Fed. Rep. of Germany

[73] Assignee: Bodenseewerk Perkin-Elmer & Co., GmbH, Uberlingen, Fed. Rep. of Germany

[21] Appl. No.: 487,635

[22] Filed: Apr. 22, 1983

Related U.S. Application Data

[63] Continuation of Ser. No. 366,636, Apr. 8, 1982, abandoned.

[30] Foreign Application Priority Data

Apr. 30, 1981 [DE] Fed. Rep. of Germany ....... 3117173

[51] Int. Cl.³ .......................................... B01D 15/08
[52] U.S. Cl. .................................. 55/386; 210/198.2; 285/156
[58] Field of Search .............. 55/197, 386; 210/198.2; 285/156

[56] References Cited

U.S. PATENT DOCUMENTS

| | | | |
|---|---|---|---|
| 3,494,174 | 2/1970 | Green et al. | 55/197 X |
| 4,083,702 | 4/1978 | Hartigan et al. | 55/386 X |
| 4,313,828 | 2/1982 | Brownlee | 210/198.2 |

FOREIGN PATENT DOCUMENTS

| | | | |
|---|---|---|---|
| 2840612 | 3/1980 | Fed. Rep. of Germany | 55/386 X |
| 561134 | 10/1977 | U.S.S.R. | 55/386 |

OTHER PUBLICATIONS

Gas Chromatography With Glass Capillary Columns by Jennings, Academic Press of N.Y., pp. 62–64, 1978.

Primary Examiner—John Adee
Attorney, Agent, or Firm—F. L. Masselle; E. T. Grimes; R. A. Hays

[57] ABSTRACT

In gas chromatography, the column ends of two capillary columns are inserted into a straight capillary from both sides forming annular gaps. The capillary is located in a tee out of which the capillary columns are sealingly guided, and to which carrier gas is supplied by means of a flushing flow conduit. A "straight-forward operation" having capillary columns connected in series and a "flush-back operation" are possible. The dead volume between the capillary columns can be kept small.

6 Claims, 5 Drawing Figures

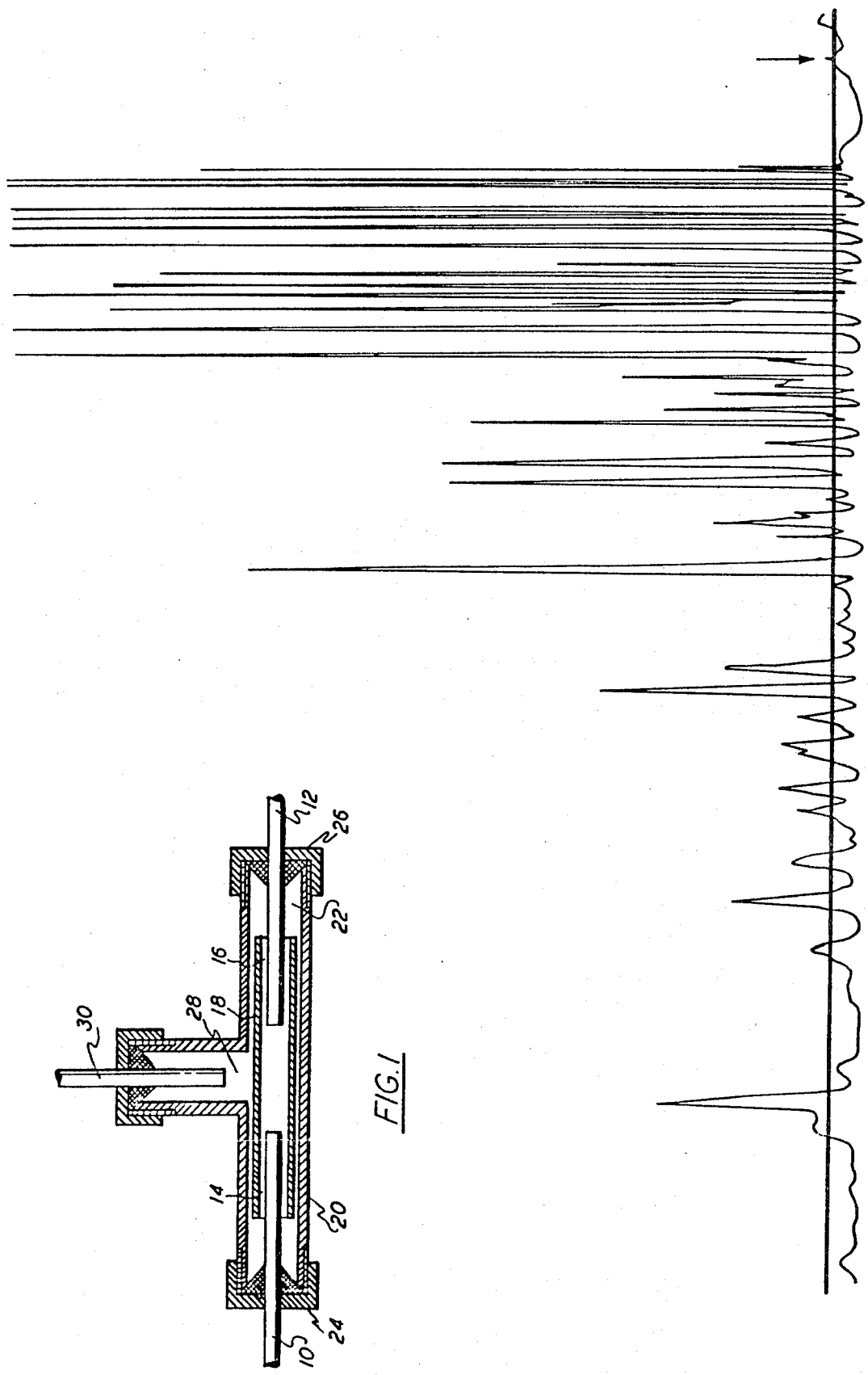

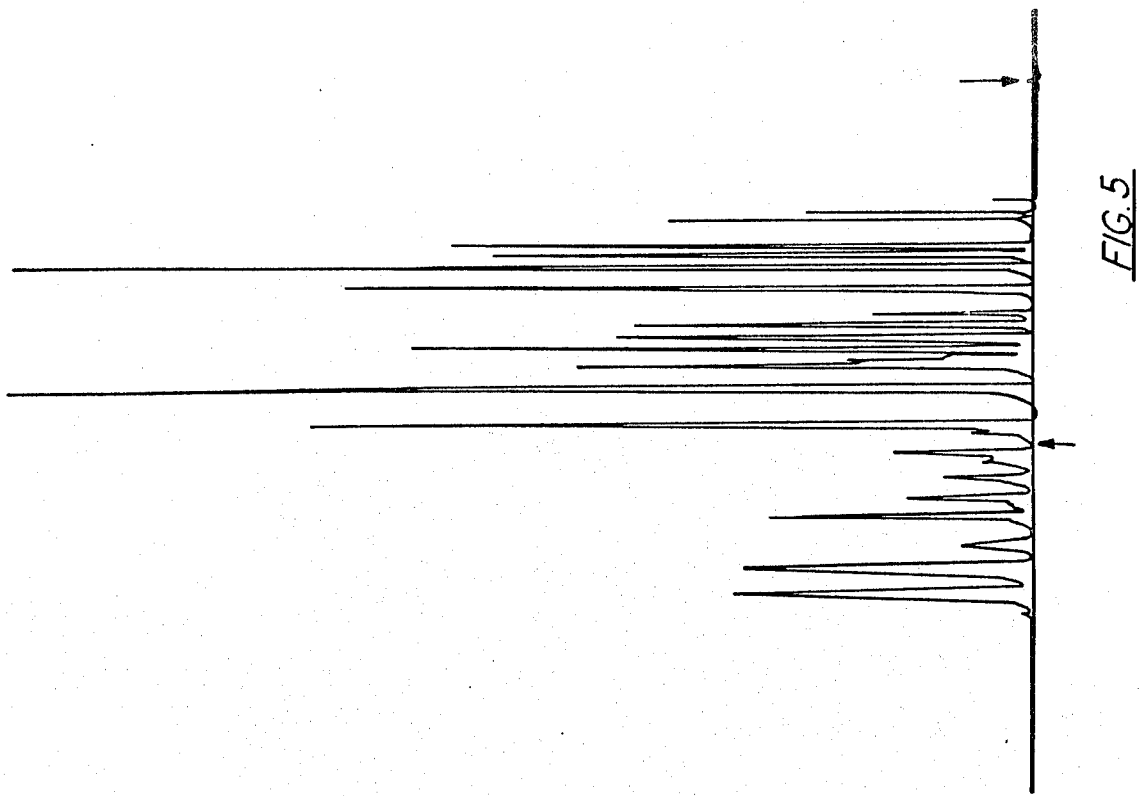
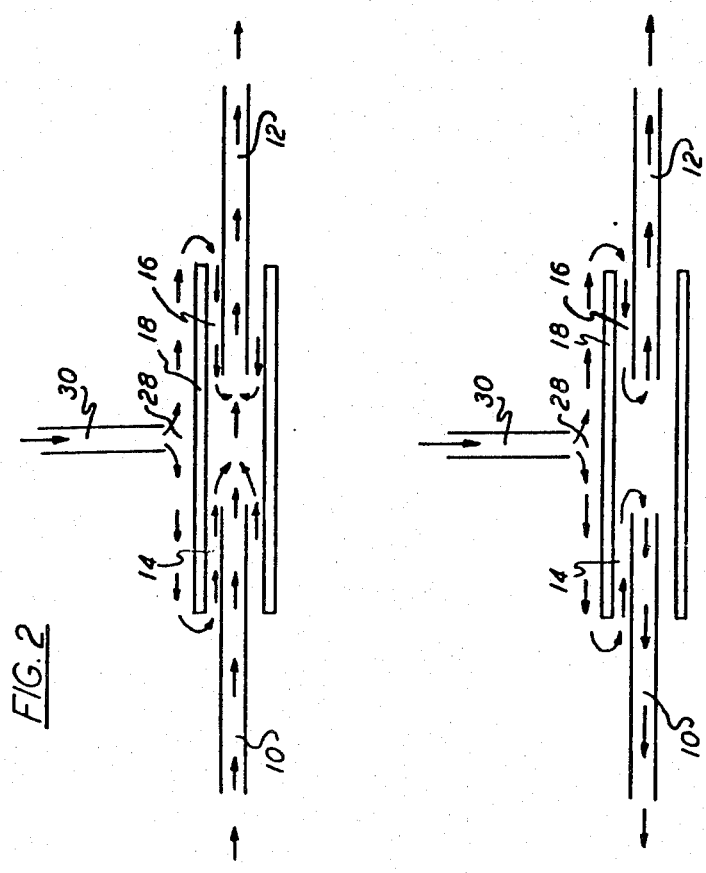

ASSEMBLY FOR CONNECTING THE COLUMN ENDS OF TWO CAPILLARY COLUMNS

BACKGROUND OF THE INVENTION

This is a continuation of U.S. patent application Ser. No. 366,636 filed Apr. 8, 1982, now abandoned.

The present invention generally relates to a connecting means useful in gas chromatography for joining the ends of two capillary columns and, in particular, relates to a connector wherein the connecting means includes a connecting piece.

A conventional connecting assembly is known from "Siemens MP 44. 1979". There, the two column ends are sealingly inserted into a sleeve-like housing. The housing is divided into two chambers by means of a central sealing piece. A platinum-iridium capillary is located in the sealing piece, which capillary extends into the column ends forming annular gaps there between. Operationally, a carrier gas is supplied to the chambers under different adjustable pressures to realize the different modes of operation, namely "straightforward operation", "cut operation" and "flushback operation". In "straightforward operation", carrier gas flows out of one of the chambers through the annular gap between the platinum-iridium capillary and the upstream capillary column into the platinum-iridium capillary. Due to this "flushing flow", the emergence of sample vapor through the annular gap into the dead volume formed within the housing is avoided. The carrier gas inserted into the other chamber flows through the annular gap formed within the upstream capillary and, also here, prevents the sample vapor emerging from the platinum-iridium capillary from entering the dead volume. Therefore, the carrier gas flow with the sample vapor is transported from the upstream capillary column through the platinum-iridium capillary into the downstream capillary column. Thus, practically only the volume of the platinum-iridium capillary is effective as dead volume.

During "flush-back operation", the pressure exerted on the first chamber is increased relative to the inlet pressure at the entrance of the upstream capillary such that a current from the first chamber of the housing through the annular gap of the upstream capillary column and, in reverse direction, through this capillary column towards its entrance occurs. In contrast to this, a current through the annular gap of the downstream capillary column and, further on, through this capillary column is produced due to the pressure exerted on the second chamber. If the upstream capillary column is a pre-column, the less volatile components of the sample, which are in the pre-column in the moment of change-over from "straight-forward operation" to "flush-back operation", are flushed back to its entrance, whereas the more volatile components, which have already been transported into the downstream main column, are further transported through the main column.

The separating procedures including pre- and main columns and including straight-forward and flushback operations are conventional techniques in packed separating columns. In using capillary columns (German patent No. 1.063.409), however, dead volumes of the connecting piece can lead to an undesired broadening of the bands and consequently to a deterioration of the separating capacity. In emerging from the pre-column, the sample vapors dissipate into the dead volume. In this case, instead of a "plug" or "packet" as narrow as possible of a pre-separated sample component, the main column contains a relatively large volume, compared thereto, of carrier gas, in which the sample components are contained in a diluted state. Therefore, efforts have to be made to keep the dead volumes formed in the connecting piece as small as possible.

In the prior art assembly discussed above, the end faces of the column ends are necessarily spaced by a relatively large distance. The dead volume is maintained small in that the connection of the capillary columns is established by means of a very narrow capillary as connecting piece. With the annular gap taken into account, the outer diameter of the capillary has to be smaller than the inner diameters of the capillary columns. A very small inner diameter of the capillary results therefrom thus introducing an unacceptable high flow resistance. Therefore, an expensive equipment for measuring and regulating the differential pressure across this capillary is provided in the prior art assembly to maintain a well-defined flow through the capillary. Furthermore, the capillary manufactured as a platinum-iridium capillary is expensive. It is often desired, however, to lead the carrier gas and sample vapor flow only through inert quartz and glass capillaries and to avoid contact with metal parts as far as possible.

SUMMARY OF THE INVENTION

Accordingly, it is one object of the present invention, to provide an assembly for connecting the column ends of capillary columns, which assembly is simply constructed, yields a small dead volume, presents small flow resistance for the carrier gas flow and can be constructed of glass or quartz components.

This object is achieved, at least in part, by means of a connecting piece including a straight capillary into which the two column ends are inserted to form annular gaps.

In that way, not a capillary is inserted into the column ends of the capillary columns as connecting piece, but the column ends are inserted into the capillary forming the connecting piece. This capillary may have a relatively large outer and inner diameter and may therefore be made of glass, for example. Further, it does not introduce any flow resistance for the carrier gas passing therethrough. The small dead volume is achieved in that the capillary column is introduced into the capillary forming the connecting piece far enough such that its end faces are located adjacent to each other. The capillaries may be coated up to column ends.

BRIEF DESCRIPTION OF THE DRAWINGS

An examplary embodiment of the present invention is described in greater detail hereinafter with reference to the accompanying drawing, which is not drawn to scale, and wherein:

FIG. 1 is a cross-sectional view of an assembly for connection capillary columns incorporating the principles of the present invention.

FIG. 2 is a flow pattern of the assembly of FIG. 1 during "straight-forward operation", in which the two capillary columns are connected in series.

FIG. 3 is a flow pattern similar to that of FIG. 2, showing the flow pattern during "flush-back operation".

FIG. 4 is a chromatogram, taken during "straight-forward operation" with two capillary columns, connected in series by means of a connecting piece.

FIG. 5 is a chromatogramm taken with the same arrangement of the same mixture (crude oil), wherein change-over to "flush-back operation" took place after eight minutes.

DETAILED DESCRIPTION OF THE INVENTION

A first capillary column, generally indicated at 10, serves as a "pre-column", whereas a second capillary column 12 serves as "main column". The two capillary columns 10 and 12 are preferably quartz or glass capillaries. The column ends are inserted into a straight capillary 18 from opposite sides, each forming therewith an annular gap 14 and 16, respectively. The capillary 18 is preferably made of glass. Means are provided for producing an inwardly directed flushing flow of inert gas (carrier gas) through the annular gaps 14 and 16. Relative to the flushing flow, the annular gaps 14 and 16 are so narrow that the flow speed of the flushing flow is faster than the diffusion rate of the sample components in the carrier gas. In this way, such sample components are prevented from diffusing into the annular gaps 14 and 16, and thereby, annular gaps 14 and 16 are eliminated as dead volumes.

The flushing-flow producing means includes a tee junction 20. The capillary 18 of the connecting piece is disposed in the part 22 corresponding to the "transverse beam" of tee 20, out of which part 22 the capillary columns 10 and 12 on opposite sides are sealingly guided by means of packings 24 and 26, respectively. The part 28 corresponding to the "vertical beam" of tee 20 is connected to a flushing flow conduit 30. This flushing flow conduit 30 is formed by a metal capillary sealingly introduced into part 28 of tee 20 by means of a packing 32.

During "straight-forward operation", carrier gas pressure is applied to the entrance of the upstream capillary column 10. A reduced carrier gas pressure becomes effective through the flushing gas conduit 30. As can be seen from FIG. 2, a flushing flow then occurs, as illustrated in dashed lines, and flowing from the flushing gas conduit 30, around the capillary 18, through the annular gaps 14 and 16 and into the downstream capillary column 12. The carrier gas and sample vapor flow from the upstream capillary column 10 also flows into the downstream capillary column 12. The flow speed of the flushing flow in the annular gaps 14 and 16 is faster than the diffusion rate of the sample vapor in the carrier gas such that no sample vapor may diffuse into the annular gaps 14, 16 or into the space outside the capillary 20. Therefore, the annular gaps 14 and 16 do not form a dead volume which might result in adversely affecting the separating capacity. Only the space between the end faces of capillary columns 10 and 12 is dead volume. This space may be made very small, if the end faces are spaced a small distance from each other. It has been found that the assembly described does not adversely affect the separating capacity.

In FIG. 3, the flow conditions during flush-back operation are illustrated. The carrier gas pressure at the entrance of the upstream separating column 10 is removed. The flushing flow continues flowing from the flushing gas conduit 30 around the capillary 18 and through the annular gaps 14 and 16. Now, however, it enters the upstream capillary column 10 at its normal exit end as well as the downstream capillary column 12. In the upstream capillary column 10 (pre-column), it causes flush back, that means, the sample components still being in this capillary column 10, are transported back to the entrance of this capillary column. The sample components in the downstream capillary column 12, the main column, continue to be transported through the capillary column and are separated as usual.

During "straight-forward operation", the two capillary columns 10 and 12 form a pressure divider, if they are connected in series with respect to flow, through which pressure divider a pressure dividing between the entrance pressure at the entrance of the upstream capillary column 10 and the atmospheric pressure at the exit of the downstream capillary column 12 is caused.

Within the capillary 20 pressure appears between the capillary columns 10 and 12 due to this pressure dividing. The pressure exerted on the flushing gas conduit 30 is selected somewhat greater than this pressure such that just the flushing flow through the annular gaps 14 and 16 is produced. If the inlet pressure at the upstream separating column 10 is removed, indeed higher flushing flows flow through the annular gaps 14 and 16. The pressure relations in the space between the end faces of the column ends within capillary 20, however, do not substantially change. The flow in the downstream capillary 12 does not change as well, thereby. The chromatographic separation of the sample continues without any change in the capillary 12.

This result can be better understood from FIGS. 4 and 5 which show the result of a head-space analysis of crude oil; once in continuous straight-forward operation and once after a change-over to flush-back operation after about 8 minutes. As capillary columns 10 and 12, two quartz capillaries each being 25 meters long were used being connected to each other by means of an assembly of the type described. The measuring was made by a Perkin-Elmer gas chromatograph Sigma 3 having a flame ionization detector. It can be seen that the appearance of the following bands is unaffected by the change-over to flush-back operation.

What is claimed is:

1. Assembly for connecting the column ends of capillary columns by means of a connecting piece in gas chromatography; said assembly comprising:
   a connecting piece; and
   a capillary tube positioned with said piece, said capillary tube being adapted to accept therein the ends of capillary columns whereby there is created annular gaps between said columns and said capillary tube.

2. Assembly as claimed in claim 1 wherein said capillary tube is glass.

3. Assembly as claimed in claim 1 further comprising:
   means for producing an inwardly directed flushing flow of inert gas through said annular gaps.

4. Assembly as claimed in claim 3 wherein:
   said capillary of said connecting piece being disposed in the part corresponding to the transverse beam of a tee, out of which said capillary columns are sealingly guided and of which the part corresponding to the vertical beam is connected to a flushing flow conduit.

5. Assembly as claimed in claim 4 wherein:
   said capillary columns are quartz capillaries.

6. Assembly as claimed in claim 5 wherein:
   said flushing flow conduit is a metal capillary.

* * * * *